United States Patent
Chen et al.

(10) Patent No.: US 9,518,927 B2
(45) Date of Patent: Dec. 13, 2016

(54) SURFACE-ENHANCED RAMAN SCATTERING SUBSTRATE AND MANUFACTURING METHOD THEREOF

(71) Applicant: National Taiwan University, Taipei (TW)

(72) Inventors: Hsuen-Li Chen, Taipei (TW); Sin-Yi Chou, Taipei (TW); Chen-Chieh Yu, Taipei (TW); Yu-Ting Yen, Taipei (TW)

(73) Assignee: NATIONAL TAIWAN UNIVERSITY, Taipei (TW)

( * ) Notice: Subject to any disclaimer, the term of this patent is extended or adjusted under 35 U.S.C. 154(b) by 53 days.

(21) Appl. No.: 14/548,286

(22) Filed: Nov. 20, 2014

(65) Prior Publication Data
US 2016/0061735 A1    Mar. 3, 2016

(30) Foreign Application Priority Data
Aug. 29, 2014 (TW) .............................. 103130033 A

(51) Int. Cl.
*G01N 21/01* (2006.01)
*G01N 21/65* (2006.01)
(Continued)

(52) U.S. Cl.
CPC ................ *G01N 21/658* (2013.01); *C22F 1/14* (2013.01); *C23C 14/205* (2013.01); *C23C 14/5813* (2013.01); *C23C 14/5873* (2013.01)

(58) Field of Classification Search
CPC ........ G01N 21/03; G01N 21/05; G01N 21/74; G01N 21/01; G02B 21/34
(Continued)

(56) References Cited

U.S. PATENT DOCUMENTS

| 2002/0110673 A1* | 8/2002 | Heydarpour ...... G02F 1/133305 428/209 |
| 2007/0042223 A1* | 2/2007 | Orimo .................... C01B 3/001 428/698 |

(Continued)

OTHER PUBLICATIONS

Highly Sensitive Surface Enhanced Raman Scattering Substrates Based on Filter Paper Loaded with Plasmonic Nanostructures by Chang H. Lee, Mikella E. Hankus, Limei Tian, Paul M. Pellegrino, and Srikanth Singamaneni; Published on Oct. 21, 2011@ dx.doi.org/10.1021/ac2016882 |Anal. Chem. 2011, 83, 8953-8958.

(Continued)

*Primary Examiner* — Tarifur Chowdhury
*Assistant Examiner* — Md M Rahman
(74) *Attorney, Agent, or Firm* — Chun-Ming Shih

(57) ABSTRACT

In a Surface-Enhanced Raman Scattering (SERS) substrate and the manufacturing method thereof, the SERS substrate includes a low thermal conductivity base and a plurality of metal nanoparticles (NPs). The surface of the low thermal conductivity substrate has a first surface, and the first surface has a plurality of ripple micro/nano structures. The plurality of metal NPs are non-continuously densely arranged on the ripple micro/nano structures of the first surface. The metal NPs have a height difference along the ripple micro/nano structures, and form a 3D electric field enhanced region. The manufacturing methods includes sputtering a metal nano-thin film on a surface of a low thermal conductivity base, and the surface of the low thermal conductivity base has a plurality of ripple micro/nano structures; using laser to ablate the metal nano-thin film; and forming a plurality of metal NPs, which are non-continuously densely arranged.

9 Claims, 18 Drawing Sheets

(51) Int. Cl.
C23C 14/58 (2006.01)
C23C 14/20 (2006.01)
C22F 1/14 (2006.01)

(58) Field of Classification Search
USPC .......................................... 356/244
See application file for complete search history.

(56) References Cited

U.S. PATENT DOCUMENTS

| | | | | |
|---|---|---|---|---|
| 2008/0170982 | A1* | 7/2008 | Zhang | B82Y 10/00 423/447.3 |
| 2008/0185951 | A1* | 8/2008 | Aurongzeb | H01J 9/042 313/326 |
| 2012/0212732 | A1* | 8/2012 | Santori | B82Y 20/00 356/301 |
| 2014/0011013 | A1* | 1/2014 | Jin | B05D 5/08 428/297.4 |
| 2015/0107273 | A1* | 4/2015 | Anantharaman | F04B 37/085 62/55.5 |

OTHER PUBLICATIONS

Paper-Based SERS Swab for Rapid Trace Detection on Real-World Surfaces by Chang H. Lee, Limei Tian, and Srikanth Singamaneni; Published on Web Dec. 3, 2010 2010 @ American Chemical Society vol. 2 • No. 12 • 3429-3435 • 2010.

Batch fabrication of disposable screen printed SERS arrays by Lu-Lu Qu, Da-Wei Li, Jin-Qun Xue, Wen-Lei Zhai, John S. Fosseyab and Yi-Tao Long extracted from Lab on a Chip Miniaturisation for chemistry, physics, biology, materials science and bioengineering vol. 12, No. 5, Mar. 7, 2012, pp. 837-996.

Highly efficient SERS test strips by Ran Zhang, Bin-Bin Xu, Xue-Qing Liu, Yong-Lai Zhang, Ying Xu, Qi-Dai Chen and Hong-Bo Sun; extracted from the Royal Society of Chemistry 2012 Chem. Commun., 2012, 48, 5913-5915 5913.

* cited by examiner

| shots of laser Ablation<br>thickness of metal thin film | One shot | Three shots | Five shots |
|---|---|---|---|
| 10nm | 41.3% | 33.9% | 25.6% |
| 20nm | 49.2% | 32.5% | 23.0% |
| 30nm | 69.4% | 31.7% | 27.0% |
| 50nm | 36.8% | 24.6% | 17.5% |

| pore size / film thickness | 20μm | 8μm | 2.5μm |
|---|---|---|---|
| 30nm | 30.3% | 49.1% | 69.4% |

FIG. 12

| Magnification | Diameter (NA) | Depth of the object (DOF, μm) | Diameter of the focused laser spot (μm) |
|---|---|---|---|
| 4x | 0.10 | 31.6 | 7.7 |
| 10x | 0.25 | 5.1 | 3.0 |
| 20x | 0.40 | 2.0 | 1.9 |
| 40x | 0.65 | 0.75 | 1.2 |
| 60x | 0.85 | 0.45 | 0.9 |
| 100x | 0.95 | 0.35 | 0.8 |

FIG. 14

SURFACE-ENHANCED RAMAN SCATTERING SUBSTRATE AND MANUFACTURING METHOD THEREOF

BACKGROUND

1. Technical Field

The disclosed example relates to a surface-enhanced Raman scattering substrate and manufacturing method thereof, particularly to a low-cost, disposable, quick made, high sensitivity and high reproducibility surface-enhanced Raman scattering substrate and manufacturing method thereof.

2. Related Art

Surface-enhanced Raman scattering (SERS) is applied to high sensitivity sensors. The SERS can quickly and immediately detect the chemical and biological molecular in the environment. The SERS has the uniqueness of the molecular spectrum of the analyte and the low analyte concentration detecting capability. The SERS does not destroy the molecule of the analyte during detecting, and the analyte does not need to be tagged either. Also, the detecting information can be obtained immediately, and the operation is simple as well.

The SERS strengthens the Raman signal by the local electric field enhancement caused by the localized surface plasma resonance (LSPR) of the metal nano structure. Nowadays, the production of the metal nano structure uses advanced micro nano processing technology to produce nano structure, such as optical lithography, focused ion beam, electron beam lithography, etc. Those processing procedures are complicated, and the costs are high and not reducible, thus limiting the application of the SERS in the related field and the SERS only being used in the laboratory. Therefore, in order to improve the processing procedure of the SERS to a simple and inexpensive processing procedure, as well as applying the SERS in the daily analyzing and on site detection to increase the application field thereof, a low-cost and easy-made SERS substrate is eagerly needed.

BRIEF SUMMARY

The disclosed example is to provide an ecofriendly, wide application, high sensitivity SERS substrate with high density metal nanoparticle. The production method of this substrate not only is fast and easy for producing, but also can be done efficiently.

The disclosed example provides a SERS substrate which includes a low thermal conductivity base and a plurality of metal nanoparticles (NPs). The surface of the low thermal conductivity substrate has a first surface, and the first surface has a plurality of ripple micro/nano structures. The plurality of metal NPs are non-continuously densely arranged on the ripple micro/nano structures of the first surface. The metal NPs have a height difference along the ripple micro/nano structures, and form a 3D electric field enhanced region.

In order to prepare the SERS substrate as described above, the disclosed example also provides the following preparation steps: sputtering a metal nano-thin film on a surface of a low thermal conductivity base, and the surface of the low thermal conductivity base has a plurality of ripple micro/nano structures; using laser to ablate the metal nano-thin film; and forming a plurality of metal NPs, which are non-continuously densely arranged.

BRIEF DESCRIPTION OF THE DRAWINGS

These and other features and advantages of the various embodiments disclosed herein will be better understood with respect to the following description and drawings, in which like numbers refer to like parts throughout, and in which:

FIGS. 3 (e)-(h) are the electron microscope images of the 10 nm, 20 nm, 30 nm, and 50 nm silver metal nano thin film on a paper of the four examples of the first preferred embodiment under one shot of the laser ablation according to the example embodiment;

FIGS. 4 (e)-(h) are the electron microscope images of the 10 nm, 20 nm, 30 nm, and 50 nm silver metal nano thin film on a paper of still another four examples of the first preferred embodiment under five shots of the laser ablation according to the example embodiment;

FIG. 6 shows the surface coverage of the silver nanoparticle on the SERS substrate of twelves examples of the first embodiment according to the example embodiment;

FIG. 11(d) is a comprehensive comparison of the nanoparticle diameter;

FIG. 12 shows the surface coverage of the silver nanoparticle of three examples of the third preferred embodiment: 20 µm, 8 µm, 2.5 µm pore size of the filter paper;

FIG. 14 shows the diameter and size of the light spot and the field depth of the object lens with different magnification for the laser with wavelength 633 nm;

DETAILED DESCRIPTION

The disclosed example uses low thermal conductivity base to restrict the laser energy to the metal thin film, only a small parts of the energy will be conducted to the low thermal conductivity base, thereby enhancing the light-heat conversion efficiency, and most of the thermal energy transformed from the laser will be conducted to the metal thin film. Paper or oxide base (such as glass) can both be the low thermal conductivity base. Paper base is used to illustrate the preferred embodiment of the disclosed example, but those low thermal conductivity bases which only conduct very small parts of the energy to further improve the light-heat conversion efficiency can be alternative replacements of the disclosed example. When the low thermal conductivity base is in use, relatively low or blank Raman background signal will not interfere with the detection and determination. Therefore, detecting the Raman background signal of all kinds of paper to select suitable material to prevent the influence of the background signal to the analyte is very necessary.

Figure 1:
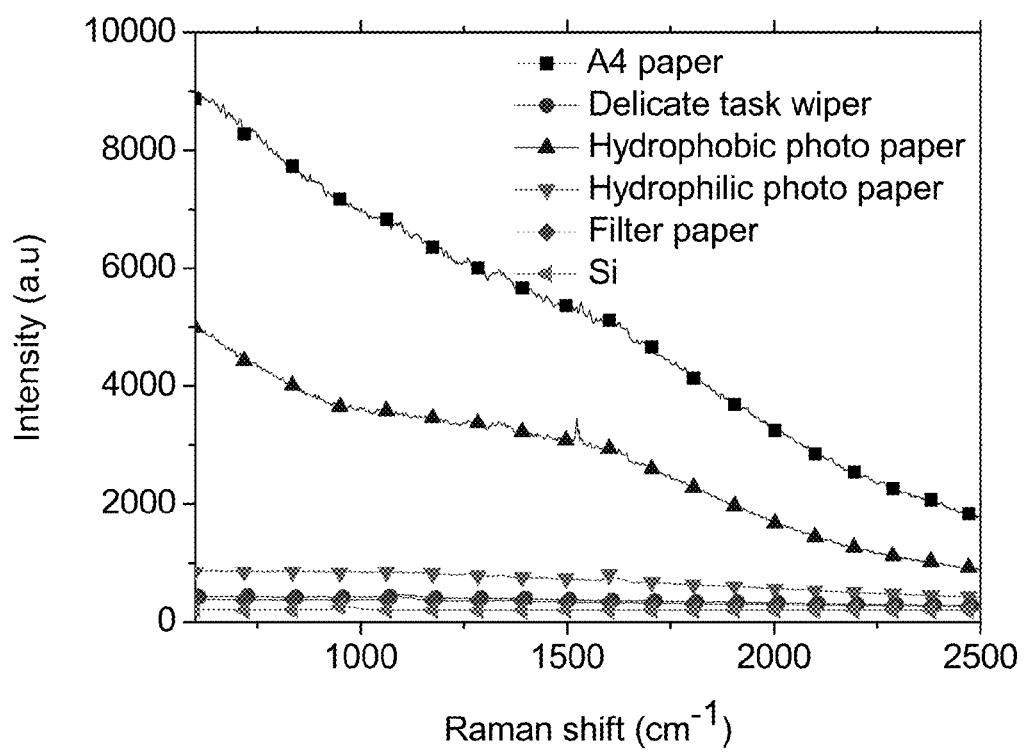
FIG. 1 is a diagram of Raman background signal of each paper substrate material according to the example embodiment.

As embodied in FIG. 1, the disclosed example tests Raman background signal to all kinds of paper base, which include filter paper, hydrophobic photo paper, hydrophilic photo paper, A4 paper, and delicate task wiper. As shown in FIG. 1, the A4 paper and the hydrophobic photo paper have the largest Raman background signal, while the filter paper and the delicate task wiper have the smallest Raman background signal. The Raman background signals of the filter paper and the delicate task wiper are small because the combinations of them are simple and no extra processing is applied to them. Besides, the function of the filter paper is to filter impurity and remain the substance needed. In order to avoid contaminating the analyte, the impurity of the filter paper combination is strictly controlled. Therefore, most of the impurity of the filter paper combination is eliminated to avoid the possibility of contamination. Even though the background signal of the delicate task wiper is also small, the quality of the delicate task wiper is not stable. Also, the structure is too loose and the texture is too soft thus easy to be damaged, which is not superior to the commercial filter paper with stable quality and unified pore size. Therefore, due to those advantages stated above, the disclosed example uses filter paper as the base for each preferred embodiment. The filter paper has pores produced by crossing fibers. In the microscopic view, those pores in the filter can be deemed as a plurality of ripple micro/nano structure, and the height difference of this structure is 100 nm-10 um.

The disclosed example uses laser thermal annealing to produce the metal nanoparticles. The metal coating films with different thickness are sputtered to the filter used as the low thermal conductivity base, and then applying laser thermal annealing thereon. The following preferred embodiments use filter paper as the low thermal conductivity base. The filter paper has pores made by crossing fibers which can influence the thickness of the metal sputtered to the filter paper, and the metal nanoparticles are eventually formed from the island shape film.

The metal nano-thin film used in the disclosed example is metal materials with localized surface plasmon resonance. When the metal nano structures close to each other, the near field and far field of the nano structure will severely influence each other, and the surface plasmon resonances will be coupled to restrict the incoming electromagnetic energy of the resonance wave band into a gap among the nano structures, thereby creating a highly localized and strengthened electric field. The area with strengthened electric field is called hot spot. The oxide of gold, silver, platinum, aluminum, or copper and the combination thereof have the aforementioned characteristic.

The following will detailedly describe the basic preparation method and testing experiment of the SERS substrate.

1. Sputtering metal nano-thin film on one side of the filter paper. Since the filter is consisted of fibers, and the surface is rough, when the metal nano-thin film is too thin, the metal thin film is not able to be formed. However, by the increasing of the thickness of the metal thin film, the metal accumulated to the island film of the filter paper fiber increased, and the metal thin film can totally cover the filter paper.

Figure 2:
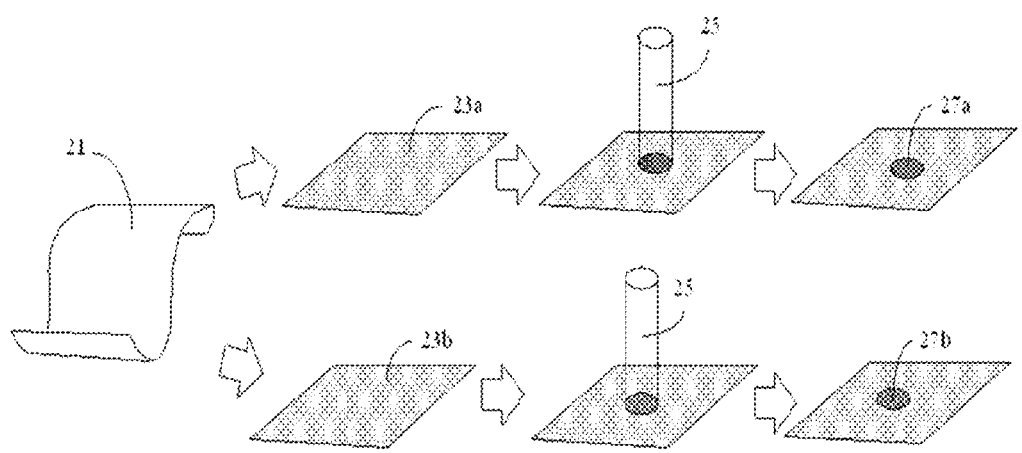
FIG. 2 is a schematic diagram of producing gold and silver metal nanoparticle on a substrate electroplated with nano metal film by the photothermal effect caused by the laser thermal annealing according to the example embodiment.

2. Laser ablating the metal nano-thin film Using KrF excimer laser with 248 nm wavelength and 125 mJ/cm$^2$ energy density under covering with one layer of quartz glass to ablate the metal nano-thin film on the surface of the filter paper, and a plurality of non-continuously and densely arranged metal nanoparticles are formed on the surface of the filter paper. The temperature of the metal thin film can reach to more than two thousands degrees, which way exceeds the melting point of gold and silver and able to melt them, and thus the metal thin film can perform the thermal annealing to form the metal nanoparticles non-continuously and densely arranged on the surface of the filter paper by the photo thermal effect. As embodied in FIG. 2, plating gold nano thin film 23a and silver nano thin film 23b on the filter paper 21, respectively, and ablating with laser 25, to form a plurality of non-continuously and densely arranged gold nanoparticles 27a and a plurality of non-continuously and densely arranged silver nanoparticles 27b. The accumulated metal nanoparticles are non-continuously and densely arranged along the plurality of ripple micro/nano structure to form the hot spot. The ripple micro/nano structure has a height difference to make the metal nanoparticles to form a 3D electric field enhanced region, thereby largely enhancing the electric field to strengthen the Raman scattering signal.

3. Plating a layer of deciduate agent to form a self-assembled film on the filter paper base to make a hydrophobic surface on the filter paper base. On the hydrophobic surface, the contact area of the droplet and the surface will become smaller significantly over time, and the solute of the droplet will be highly concentrated to a very small range, which is the so called superhydrophobic condensation effect.

The superhydrophobic condensation effect can increase concentration of the analyte and restrict the analyte to a small area.

4. Dropping 20 μL analytes with different concentration.

5. Waiting for the analytes to dry out naturally, and doing the Raman testing. Raman enhanced signal is obtained under the condition as follows: using Nikon 10× object lens with 0.25 diameters under 5 seconds integration.

Based on the above, the following paragraph will show an embodiment listing and explaining all the variables of the SERS substrate.

Figure 3:
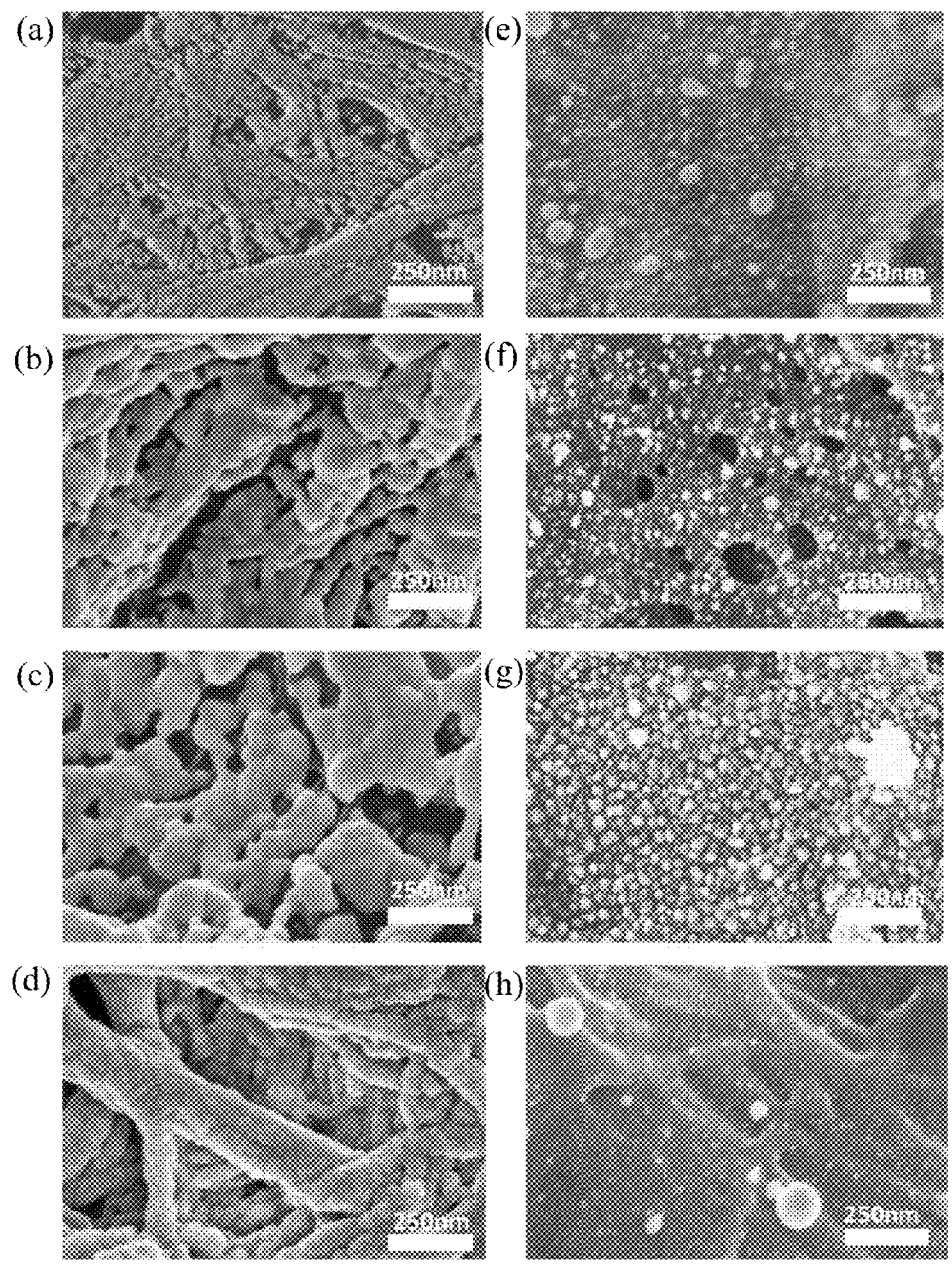
FIGS. 3 (a)-(d) are the electron microscope images of the 10 nm, 20 nm, 30 nm, and 50 nm silver metal nano thin film on a paper of the four examples of the first preferred embodiment before the laser ablation according to the example embodiment.
Figure 4:
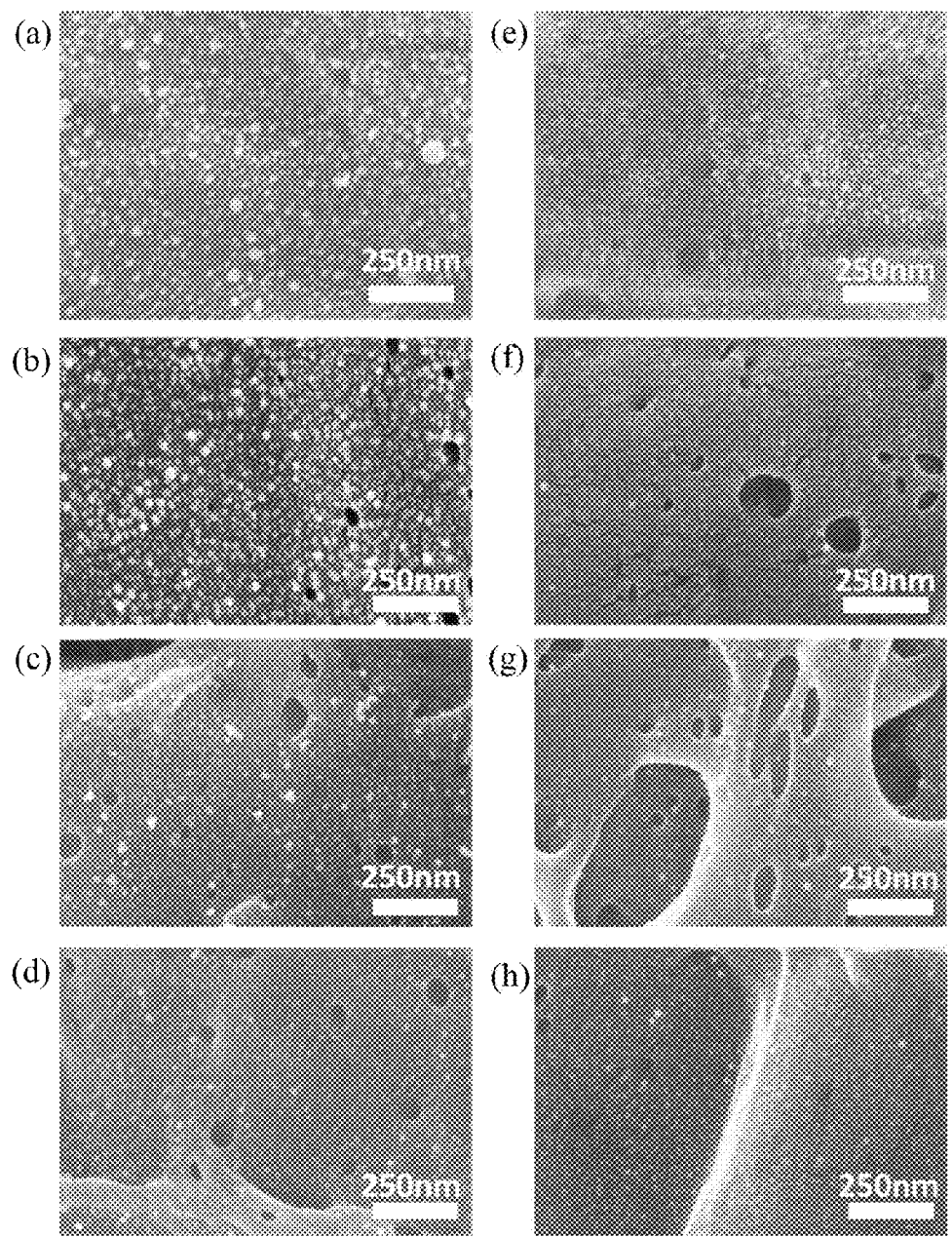
FIGS. 4 (a)-(d) are the electron microscope images of the 10 nm, 20 nm, 30 nm, and 50 nm silver metal nano thin film on a paper of another four examples of the first preferred embodiment under three shots of the laser ablation according to the example embodiment.
Figure 5:
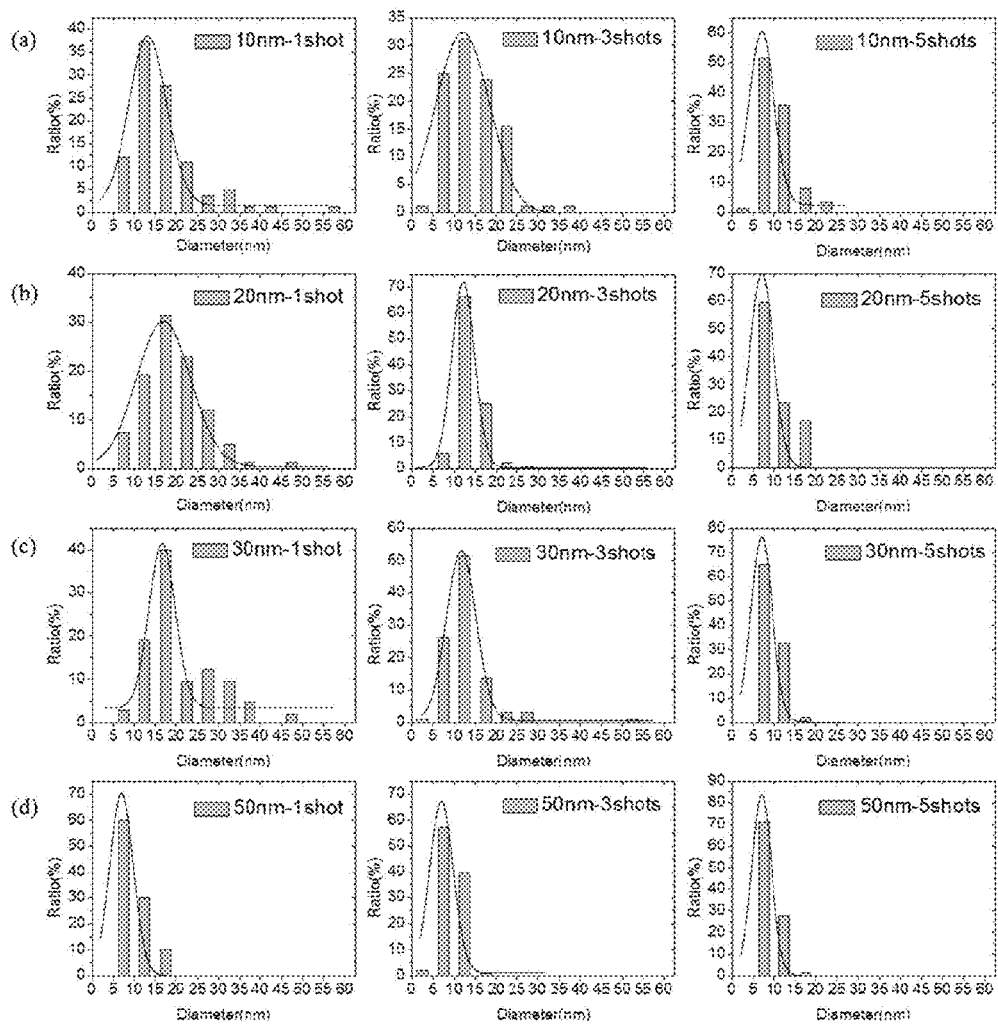
FIGS. 5 (a)-(d) are the analysis diagrams of the particle size of twelves examples of the first embodiment of the silver nanoparticle formed on 10 nm, 20 nm, 30 nm, and 50 nm silver metal nano thin film on a paper according to the example embodiment.

The first embodiment uses the thickness of the plating film and the shots of the laser ablation as the variables to derive twelves examples. In detail, the SERS substrate of the disclosed example produce the metal nanoparticles by the laser thermal annealing, Thus the metal nanoparticles will be formed from the island film, and the thickness of the metal film is between 2-20 nm. The pores formed by crossing fibers of the filter paper base can influence the plating thickness on the filter paper. Therefore, the disclosed example selects silver nano-thin film with 10 nm, 20 nm, 30 nm, and 40 nm thickness as different examples. Those silver nano-thin films with different thicknesses are sputtered on the filter paper with 2.5 μm retention diameter of the pore size to do the consequent laser thermal annealing procedure. On the other hand, by the increasing of shots of the laser ablation, the uniformity of the metal nanoparticles will be improved as well. Therefore, the disclosed example shows examples under 1, 3, and 5 shots of laser ablation. Based on two different variables shown above, the disclosed example provides twelves examples. FIGS. 3 (*a*)-(*d*) are the electron microscope images after plating the silver nano thin films with 10 nm, 20 nm, 30 nm, and 50 nm. As shown in FIGS. 3 (*a*)-(*d*), since the filter paper is consisted of fibers and the surface thereof is rough, when the film thickness is too thin, the metal film will not able to be formed. By the increasing of the plating thickness, the island film accumulated on the filter paper fibers is increased. When the plating thickness reaches 50 nm, the metal film can totally cover the filter paper. FIGS. 3 and 4 are the electron microscope images under low accelerating voltage (5 kV) before and after the laser ablation. The shape and size of the silver nanoparticles on the substrate under each parameter of the twelve examples in FIGS. 3 (*e*)-(*h*) and FIGS. 4 (*a*)-(*h*) can be observed. FIGS. 5 (*a*)-(*d*) show the particle diameter distribution of the twelve examples.

On the other hand, by the increasing of shots of the laser ablation, the uniformity of the metal nanoparticles will be improved. Therefore, the disclosed example shows three examples under 1, 3, and 5 shots of the laser ablation, respectively. However, even though the increasing of the shots of the laser ablation can also improve the uniformity of the metal nanoparticles size and distribution, the metal thin film absorbs the laser energy and the nanoparticles of the metal thin film will be dispersed in all directions due to the irregular deformation stress caused by the instant high heat. Therefore, when the shots of the laser ablation increases, the dispersed nanoparticles will increase as well, which lowers the coverage of the nanoparticles on the filter paper, and also influences the distance among all the nanoparticles. In other words, by the increasing of the shots of the laser ablation, the distribution of the nanoparticles will be wide, and the distance among the nanoparticles will be increased. The intensity of the coupling electric field is in an inverse ratio with the distance among the nanoparticles, therefore when the distance among the nanoparticles gets longer, the electric field among the nanoparticles will be weak accordingly. By Contrast, the intensity of the Raman signal is in quartic direct propagation to the intensity of the electric field, thus, the sparse nanoparticles will cause low intensity of the Raman signal. Therefore, even though increasing the shots of the laser ablation can increase the uniformity of the nanoparticles, the nanoparticles with high density cannot be achieved. In order to decrease the distance among the nanoparticles to increase the intensity of the electric field, the example with one shot of laser ablation can get the shortest distance among the nanoparticles.

As shown in the electron microscope images after the laser ablation and the particle diameter distribution diagram of all the examples, it can be found that the size of the silver nanoparticles in all the examples of the present embodiment is among 10-30 nm. By the increasing of the shots of the laser ablation, more energy will be provided to the nanoparticles to form smaller nanoparticles, which can be observed from the electron microscope images and the particle diameter distribution diagram. The ratio of the nanoparticles with small particle diameter is eventually increased. Besides, the increasing of the shots of the laser ablation can also improve the size and uniformity of the nanoparticles, and the average particle diameter will decrease. The metal thin film absorbs the laser energy and the nanoparticles of the metal thin film will be dispersed in all directions due to the irregular deformation stress caused by the instant high heat. Therefore, when the shots of the laser ablation increases, the dispersed nanoparticles will increase as well, which also lowers the coverage of the nanoparticles on the filter paper. FIG. 6 shows the surface coverage of the silver nanoparticles on the SERS substrate for each example. The shots of the laser ablation and the thickness of the metal thin film both influence the distance among the nanoparticles.

It can be observed in FIGS. 3 and 4, by the increasing of the shots of the laser ablation, the sparse distribution of the nanoparticles can increase the distance among the nanoparticles. The intensity of the coupling electric field is in an inverse ratio with the distance among the nanoparticles, therefore when the distance among the nanoparticles gets longer, the electric field among the nanoparticles will be weak accordingly. By Contrast, the intensity of the Raman signal is in quartic direct propagation to the intensity of the electric field, thus, the sparse nanoparticles will cause low intensity of the Raman signal. Therefore, even though increasing the shots of the laser ablation can increase the uniformity of the nanoparticles, the nanoparticles with high density cannot be achieved. In other words, the shots of the laser ablation have a limit. Under the highest shots of the laser ablation, the metal nanoparticles obtained have the smallest particle diameter and have even size, but the distribution of the metal nanoparticles have a smallest coverage and a lowest density, which means the weakest Raman signal intensity in the disclosed example.

Therefore, in order to decrease the distance among the nanoparticles to increase the intensity of the electric field, the example with one shot of laser ablation can get the shortest distance among the nanoparticles. As shown in FIGS. 3 (*e*)-(*h*), by the thickness changing of the metal film, the coverage and density of the nanoparticles will have an optimized parameter. In other words, the metal nano-thin film of the disclosed example has a best thickness, and the metal nanoparticles have a largest coverage and a highest density. In the present embodiment, when the metal film is thick, the material that can be provided to form metal nanoparticles is sufficient, which causes the amount of the metal nanoparticles increased and the density of the nanoparticles is increased as well. However, when the thickness of the metal film reaches 50 nm, as shown in FIG. 3 (e), most of the metal films laser ablated are formed as micro scale metal particles due to too many material sources, and the size of the rest of the nanoparticles become small and sparsely distributed. When the thickness of the metal film is 30 nm, the metal nano-thin film can form a non-continuous metal sheet shaped island film on the filter paper, and a better result can be achieved as well. Therefore, in the best example of the present embodiment, as shown in FIG. 3 (g), the metal nanoparticles on the filter paper reach the highest density and the largest coverage. The nanoparticles are densely arranged, and most of the distances among the metal nanoparticles are less than 5 nm. Due to the compact and densely stacking, the coupling electric field among the nanoparticles can be largely strengthened, and the Raman signal can be enhanced as well. Therefore, the consequent embodiment will be described according to the best example parameter: 30 nm metal film with one shot of laser ablation.

Before doing the Raman signal test, as described above, hydrophobic surface can highly concentrate the solute of the analyte into a very small area, which is called superhydrophobic concentration effect, and this effect can be applied to concentrate the concentration and restrict the area of the analyte. Therefore, after preparing the SERS filter paper base, a layer of deciduate agent (Trichloro silane perfluorooctane, PFOTCS) is plated to form a self-assembled film to make a hydrophobic surface.

All the SERS substrates need to be plated with the deciduate agent before being test. In order to verify the advantages and the disadvantages of the SERS substrate prepared with nanoparticles under each different parameter, the second preferred embodiment is going to use the optimized parameters: metal film thickness 30 nm under one shot of laser ablation, and separate the parameters into two parts: same metal film thickness and the same shots of the laser ablation.

Figure 7:
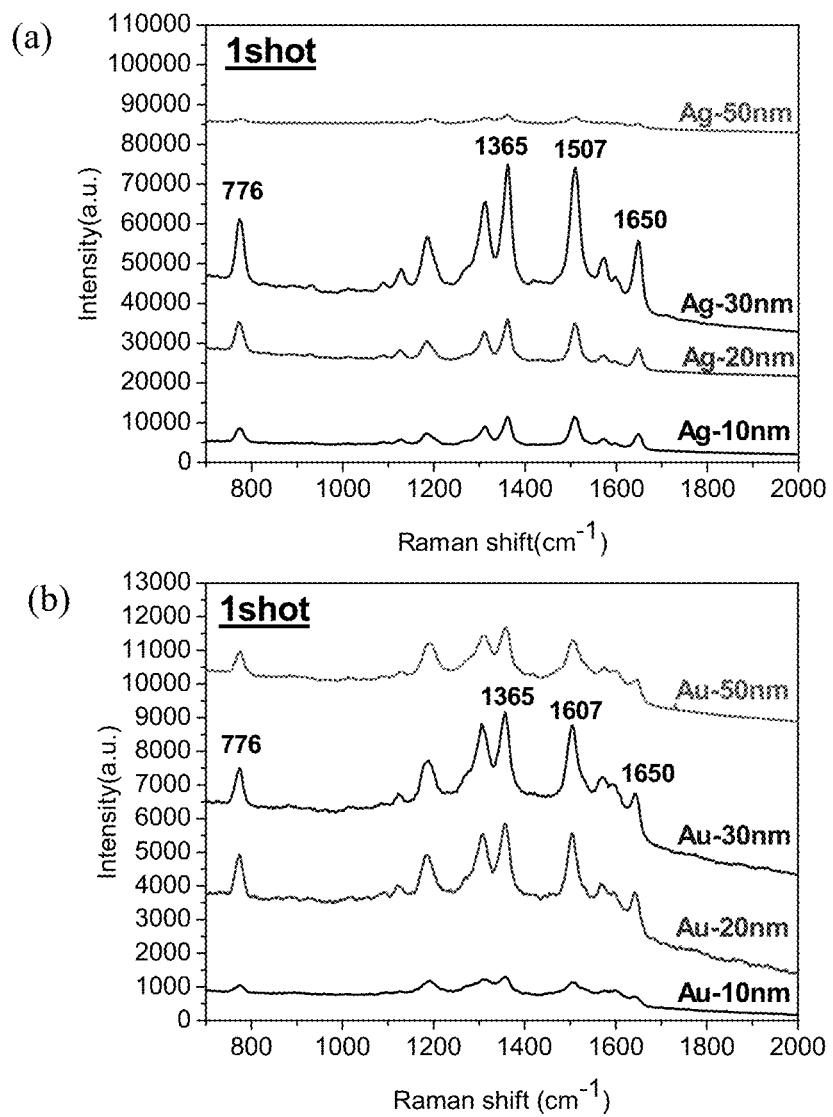
FIGS. 7 (a)-(b) are the eight examples of the second embodiment, which show the Raman signals of the silver nanoparticle and gold nanoparticle under different metal film thickness and the same shots of laser ablation.

First, the following examples discuss different metal film thickness under one shot of laser ablation. The fabrication of the eight examples of the present preferred embodiment is to sputter gold and silver nano-thin film with 10 nm, 20 nm, 30 nm, and 50 nm thickness, respectively. As described in the previous embodiment, changing the metal film thickness will influence the shape and size of the metal nanoparticle, and the influence will also influence the performance of the SERS substrate. The difference of the Raman signals are obtained by comparing the Raman signal of the Rhodamine 6G (R6G) solution with $10^{-5}$ M concentration under 5 seconds intergration, and the results are shown in FIG. 7.

The FIGS. 7(a)-(b) are the results of eight different examples under the parameters as follows: different metal film thickness with one shot of laser ablation on the silver nanoparticles and the gold nanoparticles on the filter paper. As shown in the FIGS. 7(a)-(b), the SERS effect of the silver nanoparticle is better than that of the gold nanoparticle. Silver has better metallicity than gold, which leads to a better SERS effect for silver nanoparticle. Not only the intensity of the Raman signal of silver is better than gold, the wavecrest resolution of the SERS substrate made by silver nanoparticle is better than that of gold as well. By the increasing of the metal film thickness, the nanoparticle coverage can be increased, the distance among the nanoparticles is shortened, the coupling electric field is increased, and the Raman signal is enhanced.

Following are the examples of the present preferred embodiment experimented under the parameters: sputtering gold metal nano-thin film and silver nano-thin film on a surface of the filter paper with film thickness 30 nm, and applied with one, three, and five shots of laser ablation. As described in the previous embodiment, changing the shots of the laser ablation will influence the shape and size of the metal nanoparticle, and further obtaining six examples with different SERS substrate performance. The difference of the Raman signals are obtained by comparing the Raman signal of the Rhodamine 6G (R6G) solution with $10^{-5}$ M concentration under 5 seconds intergration, and the results are shown in FIG. 8.

Figure 8:
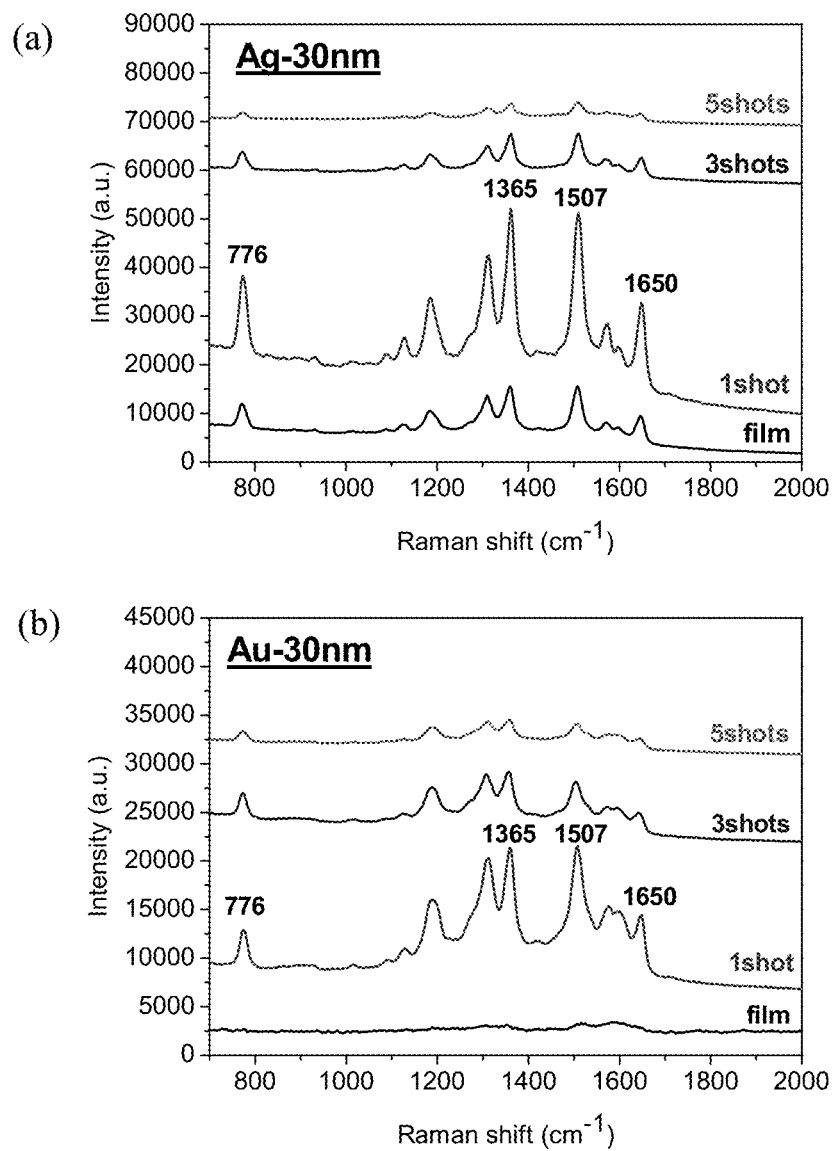
FIGS. 8 (a)-(b) are the six examples of the second embodiment, which show the Raman signals of the silver nanoparticle and gold nanoparticle under the same metal film thickness and different shots of laser ablation.

It can be observed in FIGS. 8 (a)-(b), the examples under the one shot of laser ablation can obtain the silver nanoparticles and gold nanoparticles with strongest Raman signal. After the metal film absorbs the laser energy, the deformation stress caused by the laser energy can force the nanoparticles to disperse in all directions, and thus resulting the decreasing of the nanoparticles on the filter paper base. Due to the weakening of the coupling electric field, the Raman signal is weakened as well. By the increasing of the shots of the laser ablation, the intensity of the measured Raman signal goes down accordingly. Besides, before the laser ablation, only the substrate with sputtered film can enhance the Raman signal, because the surface of the filter paper is rough, which is not formed with a nano-thin film, and a non-continuous island film with rough nano structure is formed instead. The rough nano structure can also have a hot spot effect to enhance the electric field, thereby increasing the intensity of Raman signal.

Figure 9:
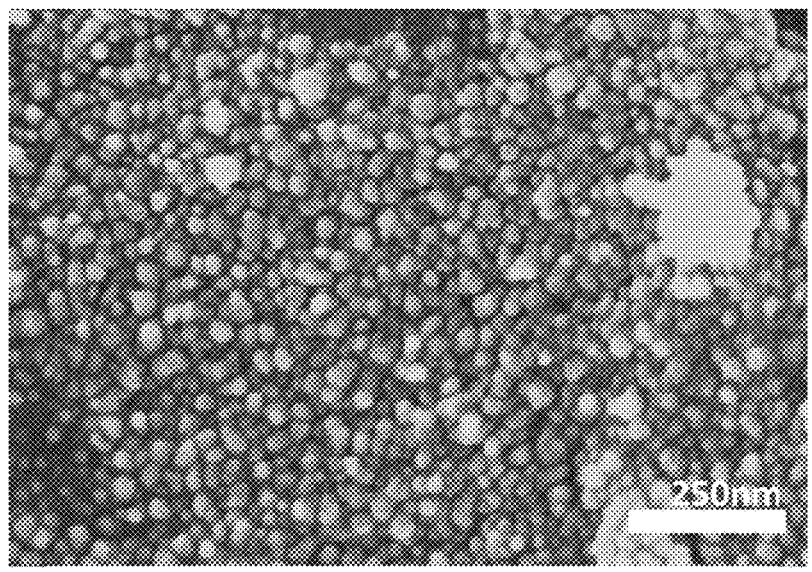
FIGS. 9 (a)-(b) are the electron microscope images of the silver nanoparticle and gold nanoparticle on the film of 30 nm thickness and under one shot of laser ablation.
Figure 9:
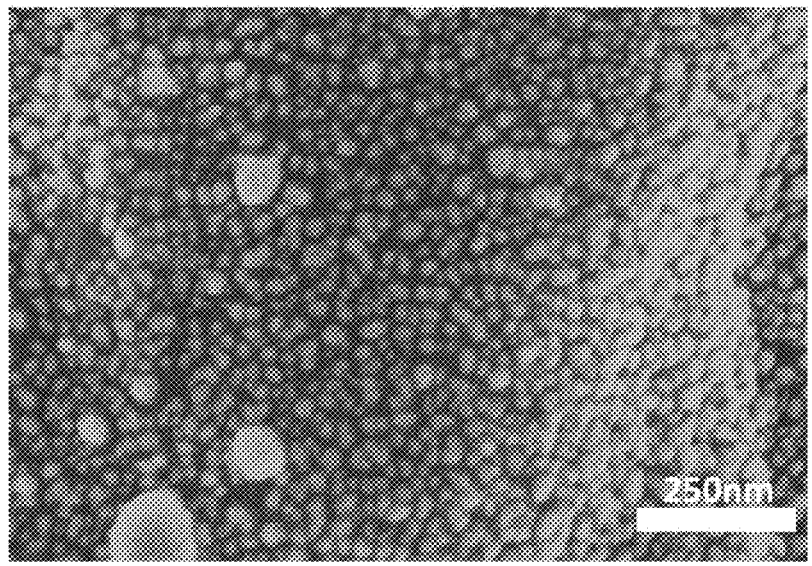

The aforementioned embodiments showing the examples of the silver nanoparticles on the filter paper. FIGS. 9 (a)-(b) show gold nanoparticles and silver nanoparticles under the same parameters as the silver nanoparticles: metal film thickness 30 nm with one shot of laser ablation. Both the silver and gold have high density nanoparticle arrangement, therefore creating sufficient electric filed enhancement to obtain stronger Raman signal.

Figure 10:
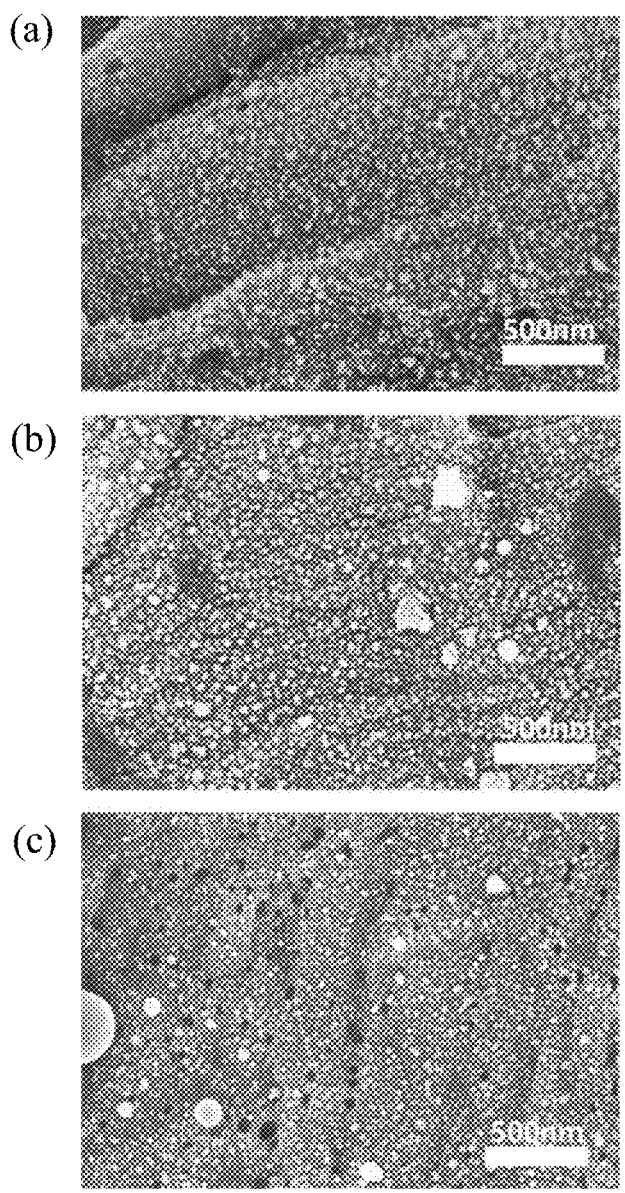
FIGS. 10 (a)-(c) are the electron microscope images of the silver nanoparticle of three examples of the third preferred embodiment: 20 µm, 8 µm, 2.5 µm pore size of the filter paper, 30 nm thickness silver nano-thin film with one shot of laser ablation.
Figure 11:
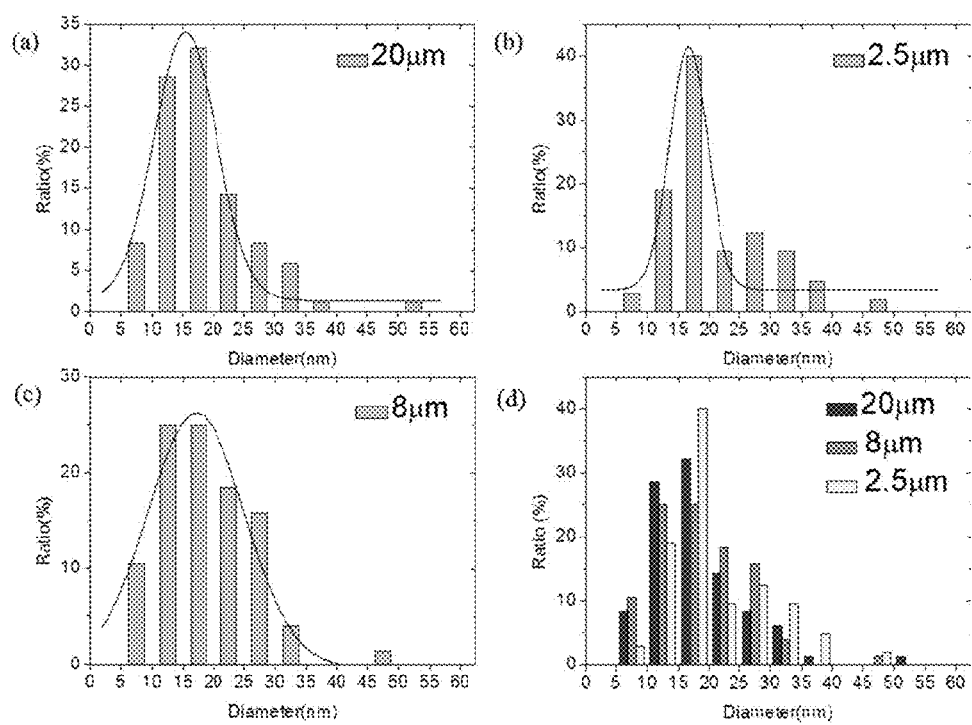
FIGS. 11 (a)-(c) are the diameter of the silver nanoparticle of three examples of the third preferred embodiment: 20 µm, 8 µm, 2.5 µm pore size of the filter paper with 30 nm thickness silver nano-thin film and one shot of laser ablation.

As described above, the present embodiment uses filter paper as the base of the SERS substrate. The filter paper has many kinds of retention pore diameter, thus the third preferred embodiment shows the influence of the filter paper pore size to the nanoparticles which is provided on the filter paper by laser thermal annealing. The three examples of the third preferred embodiment select filter paper (Whatman® No. 40, No. 41, No. 42) with retention pore size of 8 μm, 20 μm, 2.5 μm. For convenience, the following paragraph uses pore size to represent the different parameters. As described in the previous embodiment, metal film thickness 30 nm with one shot of laser ablation can obtain the metal nanoparticle array with the largest coverage and highest density. Due to the enhancement of the coupling electric field, strong Raman signal can be obtained. Therefore, the parameters of the three examples of the preferred embodiment are set as follows: sputtering metal film of 30 nm thickness with one shot of laser ablation on filter papers with different retention pore sizes. As shown in FIGS. 10 (a)-(c), from the top to the bottom shows electron microscope images of pore size 20 μm, 8 μm, and 2.5 μm. FIGS. 11 (a)-(d) show the distribution and comparison of the nanoparticle pore size. FIG. 12 shows the filter paper with different pore size, and the nanoparticle coverage thereof. As shown in the electron microscope images in FIGS. 10 (a)-(c), under the same metal film thickness, the nanoparticles formed on filter paper with bigger pore size are few and scattered, and the particle size is smaller as well. The bigger the micro scale pore size of the filter paper is, the more metal film will be sputtered into the pores, and the metal film on the surface of the filter paper will be dispersed. Therefore, the thickness of the metal film actually covering the surface of the filter paper is thinner than the idea thickness, and thus causing decreasing of the nanoparticles. After the laser ablation, the nanoparticles formed are small and has low coverage. Comparing one of the examples of the present embodiment (the size and shape of the nanoparticles of the filter paper with bigger retention pore size, as shown in FIG. 10 (*a*)) with one of the examples of the first embodiment (smallest retention pore size, metal film thickness 20 nm, one shot of laser ablation, as shown in FIG. 3 (*f*)), it can be seen that the distribution of the nanoparticles for both aforementioned examples are very similar. Further comparing the diagram of the particle diameter distribution (the leftest of FIG. 5 (*b*) and FIG. 11 (*a*)), the ratio of the particle diameter distribution for both aforementioned examples are very similar too.

Figure 13:
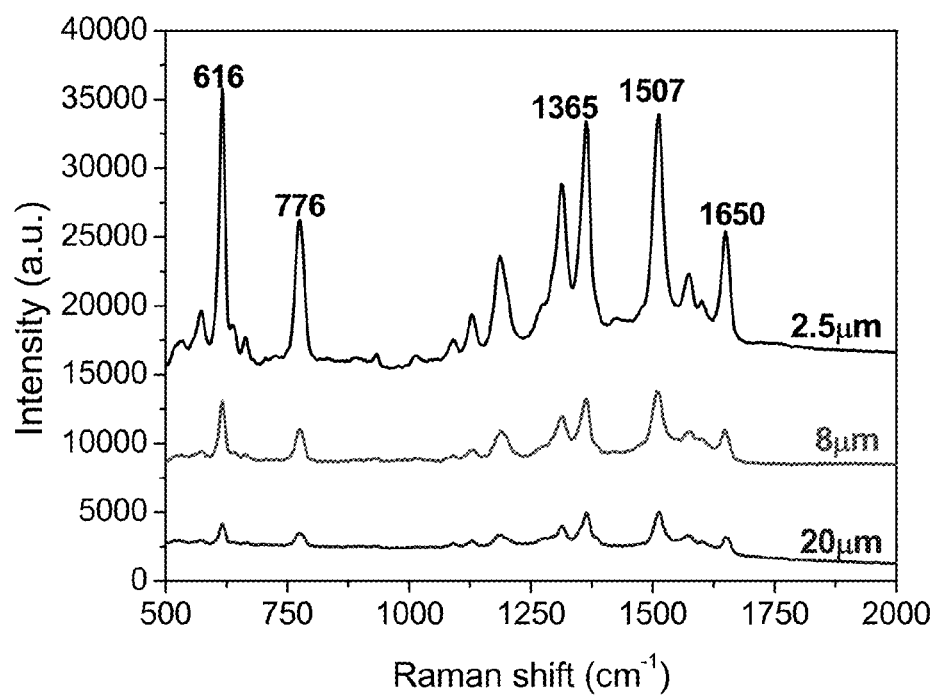
FIG. 13 is the Raman spectrum of the silver nanoparticle of the third preferred embodiment using filter paper with different pore size and with metal film thickness 30 nm, and applied one shot of laser ablation.

It can be seen from the FIG. 12, by the increasing of the pore diameter of the filter paper, the coverage of the metal nanoparticles decreases accordingly, and the distance among the metal nanoparticles is shortened, thereby weakening the coupling electric field. As shown in FIG. 13, by the pore size increasing of the filter paper, the intensity of the Raman signal decreases, showing the intensity decreasing of the electric field. Based on the experiment results of each example, the plating film thickness on the filter paper can be better controlled by the filter paper with small pore size, and the metal film can be prevented to be plated into the pore, thus further controlling forming densely arranged nanoparticles accumulated on the surface of the filter by laser thermal annealing.

Compared with the conventional technology, this disclosed example uses filter paper as the base of the SERS substrate, and the Raman signal intensity is 8 times and 3 times stronger than the silicon board and the glass board, showing the superior SERS effect by forming the nanoparticles on the paper base. The reasons why different base materials have such a big difference in Raman signal intensity lies in the special fiber structure of the paper base. The nanoparticles formed on the paper base by the laser thermal annealing have particle diameters around 10 nm to 50 nm, preferably around 10 nm to 30 nm and densely arranged. By this arrangement, the coupling electric field enhancement of the localized surface plasma resonance can be stronger. By contrast, the nanoparticles formed on the silicon board usually have the size around 200 nm to 900 nm; the localized surface plasma resonance thereof is in the field of visible light and thus is not noticeable. The metal particles are largely dispersed and the intensity of the coupling electric field is not strong either, which lowers the electric field enhancement. On the other hand, for the glass board, even though the density of the metal nanoparticles on the glass board is high, there are still many big size metal particles exist on the surface of the glass board. Therefore, except for the unnoticeable localized surface plasma resonance, the hot spot that generated by the small size particles will decrease as well, and the electric field enhancement will decrease accordingly.

Under the same fabrication condition, the difference of size and shape of nanoparticles formed on different base mainly is controlled by the thermal conductivity and roughness of the base. The thermal conductivity of the silicon board, the glass board, and the paper base are 142.2 W/mK, 0.92 W/mK, and 0.15 W/mK. In order to transform the laser energy to the thermal energy to provide energy to the metal film in the process of forming nanoparticles by laser thermal annealing, the thermal energy transferring plays a very important role. When the thermal conduction of the base is low, the energy dissipates from the base is low as well, and thus most of the thermal energy will be retained in the metal film, so as to improve the light-heat conversion efficiency. Therefore, it is presumed that the thermal conduction of the paper base itself is very low, and the metal film after being sputtered is usually non-continuous metal film, thus the thermal energy cannot be transferred to other places by the base or the metal film, and the thermal energy can be absorbed by the metal film. Therefore, there is sufficient energy to form the high density nanoparticles under only one shot of laser ablation. On the contrary, the silicon board has good thermal conductivity, thus ten shots of laser ablation is required to form the nanoparticles, and the low light-heat conversion efficiency is proved. Besides, since the paper base has rough fiber structure, the metal film formed at the sputtering process is non-continuous film, as shown in FIGS. 3 (*a*)-(*d*). When doing the laser ablation, the nanoparticles have more nucleation points, and thus only one shot of laser ablation can form large amount and densely arranged metal nanoparticles. Compared with the silicon board and the glass board, since the surfaces of the silicon board and the glass board are flat, the metal films sputtered on the surfaces will be continuous metal films, which do not have rough area to be the nucleation point. Therefore, multiple shots of the laser ablation are needed to destroy the flat metal film and make the film discontinuous to generate more nucleation points to form metal nanoparticles. The aforementioned phenomenon shows the roughness of the base determines the roughness of the metal film sputtered on the base, and also influences the number of the nucleation points of the metal nanoparticles formed by the laser thermal annealing. Therefore, all the embodiments in the disclosed example using paper as the base to produce nanoparticles by laser thermal annealing is a fast and an efficient way, and applying the paper base in SERS technology can largely enhance the Raman signal intensity.

During the Raman testing, using optical microscope to focus the laser beam into a light spot on the substrate, and then collecting the scattered light to obtain Raman scattering signal. Therefore, the depth of field (DOF), spot size, and the interaction with the substrate, can influence the collecting effect of the Raman signal. The so called DOF, means in a specific range of the focus plate, the area that clear image can be seen after the light being focused. The formula is shown as:

$$DOF = \frac{n\lambda}{2NA^2},$$

the DOF represents the depth of field; n represents the incident medium refractive index; λ means wavelength of incident light; NA means the numerical aperture of the objective lens. The size of the focusing light spot is the light spot after the laser beam being focused, and the formula is:

$$d = \frac{1.22\lambda}{NA},$$

the d means the diameter of the focused laser spot; λ means wavelength of incident light; NA means the numerical aperture of the objective lens. Due to the measuring limitation of the optical system, when measuring the Raman signal enhancement, only the signal in the range of DOF can be measured, and the DOF can be deemed as the effective Raman signal enhancement area. FIG. 14 shows the diameter and size of the light spot and the field depth of the object lens with different magnification for the laser with wavelength 633 nm.

All embodiments of the disclosed example use paper as the base of the SERS substrate. The surface of the special fiber structure of the paper is a ripple nano structure formed by the rough folded micro fiber with minor undulation. The height difference of the ripple structure is between 100 nm to 500 nnm. When using laser thermal annealing to produce metal nanoparticles on the ripple structure, the metal nanoparticles are non-continuously and densely arranged along the rough ripple micro/nano structure. The density of the metal nanoparticles in the space is decreased toward the surface of the filter paper where no metal nano-thin film is sputtered thereon. By doing so, the metal nanoparticles are arranged to form a quasi 3D structure, which increases the space density of the metal nanoparticles. Thus, not only the X axle and the Y axle of the electric field can couple as the planar structure, but also a Z axle direction is provided to be coupled with the X axle and the Y axle, to form a 3D electric field enhancement area. The intensity of the electric filed of the 3D electric field enhancement area is decreased toward the surface where no metal nano-thin film is sputtered thereon. This kind of 3D electric field enhancement area increases the space intensity of the hot spot, and thus the electric field enhancement is largely increased as compared to the planar structure, and the Raman enhancement factor increases as well. Besides, the fibers of the paper base cross to form web shape pore structure, when the metal film is sputtered thereon, part of the metal films will enter the pores, and thus the under layer fibers below the surface also have the metal nanoparticles distributed thereon after the laser thermal annealing. The object lens used in the present embodiment has 10× magnification, and the DOF of the Raman testing is about 5 µm, as shown in FIG. 14. Even though the metal nanoparticles on the focusing planar can provide largest signal enhancement, part of the metal nanoparticles in the DOF can also contribute to the electric field enhancement, thus the disclosed example can obtain stronger Raman signal.

Compared with the conventional dip coating method to prepare the SERS substrate on the paper base, the dip coating method spends more than one day for the preparation, and the dipping causes the nanoparticles cover the whole filter paper and the thickness of the nanoparticles is the same as the filter paper. However, the thickness of the ordinary filter paper is in mini meter scale (mm), and the DOF of the Raman measuring is several hundred nanometers, which is in nano meter scale (nm) to micro meter scale (µm), as shown in FIG. 14. Therefore, for the nanoparticles distributed out of the DOF, not only the lights cannot be focused to enhance the coupling of the electric field, but also not be able to collect the Raman signal. The SERS substrate of the disclosed example, most of the metal nanoparticles are distributed inside the 3D electric field enhancement area. In the DOF of the disclosed example, the amount of the metal nanoparticles distributed in the DOF is larger than those outside the DOF. Therefore, compared with the disclosed example using laser thermal annealing to produce the SERS substrate, the dip coating method is time consuming and is low efficiency, and thus the preparation process is not cost-effectiveness.

Figure 15:
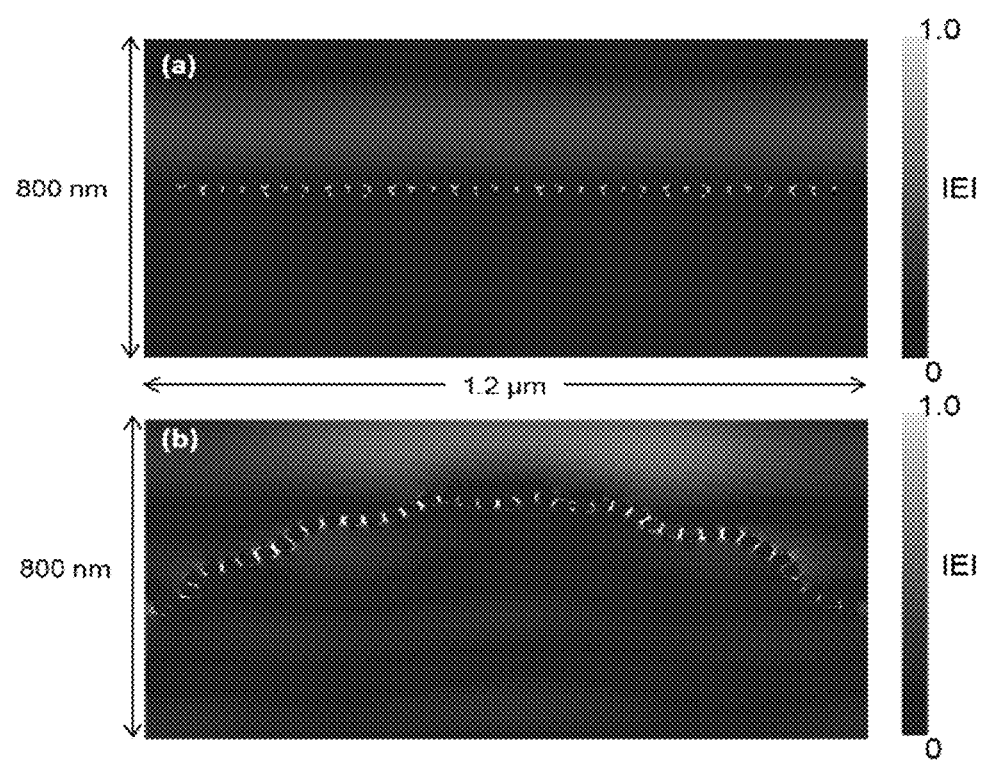
FIGS. 15 (a)-(b) shows simulated 2D plane structure and the first preferred embodiment of the example embodiment; the comparison of the diagram of the electric field intensity when the SERS substrate is placed with 30 nm silver nanoparticle at 633 nm wavelength.

A result of the simulation as shown in FIG. 15, the 2D structure is shown in FIG. 15 (*a*), and the quasi-3D structure is shown in FIG. 15 (*b*). Placing 30 nm silver nanoparticles on the 2D structure and the quasi-3D structure respectively, each particle is spaced apart from each other in 5 mm, and the silver nanoparticles are sequentially placed on the 2D structure and the quasi-3D structure until the surface thereof are fully occupied. And then, using a light source with 633 nm wavelength to perform the simulation. According to the simulation result, the brighter area represents the area with strongest electric field amplitude. As shown in FIGS. 15 (*a*)-(*b*), it can be seen that the areas among the metal nanoparticles are brighter, which means the electric field is strong, and that is where the hot spot is situated. The 3D structure in FIG. 15 (*b*) uses fiber woven filter paper with 1-2 micro meter diameters as the base, and there is a rough ripple nano structure provided thereon with metal nanoparticle densely arranged thereon as well. After comparing the simulation diagram with different structures, it can be easily seen that due to the presenting of the quasi-3D structure, the metal nanoparticles will densely arranged along the quasi-3D structure. Compared to the simple 2D planar structure, the metal nanoparticles using the filter paper as the base of all the embodiments of the disclosed example have higher space density in the DOF, which means the hot spot density of the electric field enhancement can be increased, and the electric field enhancement can be larger than the simple 2D planar structure. By using the optical simulated electric field map, it can be more specifically shown that the special rough fiber structure of the filter paper used in all embodiments of the disclosed example can increase the density of the metal nanoparticles accumulated on the filter paper, and the amount of the hot spot can be further increased to achieve better Raman signal enhancement effect. Besides, since the micro fiber structures of the filter paper are all in the DOF range, the electric field enhancement generated by the metal nanoparticles distributed on the filter paper can all be collected, thereby reaching the effect of Raman signal enhancement.

Figure 16:
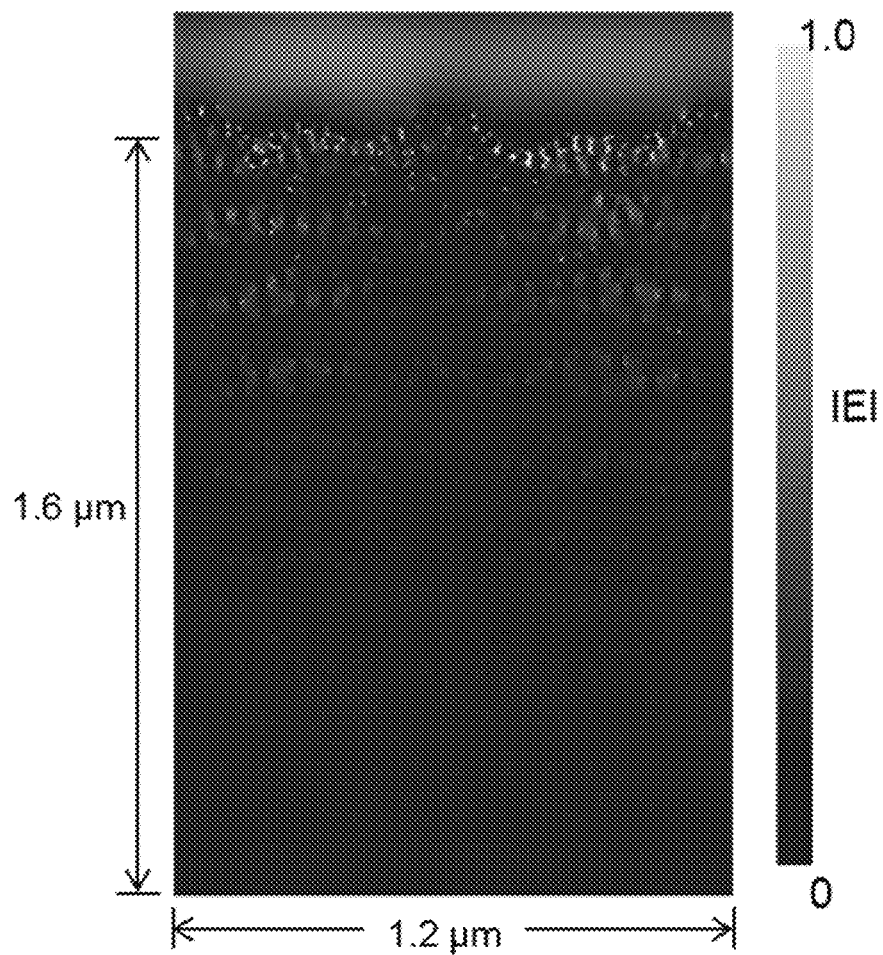
FIG. 16 is the diagram of the electric field intensity at 633 nm wavelength of placing the SERS substrate made by simulating the conventional immersion coating method with 30 nm silver nanoparticle.

Besides, using the dip coating method to produce the SERS substrate on the paper base is simulated, and the result is shown in FIG. 16. Since the nanoparticles are distributed on the whole filter paper with millimeter scale thickness, the silver nanoparticles in 30 nm size are densely arranged onto the whole paper fiber to do the simulation process. As shown in FIG. 16, the metal nanoparticles of the SERS substrate produced by the dip coating method distribute very deep. Therefore, when the light enters to the interior of the paper, the light intensity has largely decreased, and thus further decreasing the electric field enhancement. As shown in FIG. 16, when the depth exceeds 1 µm, the electric field enhancement generated by the silver nanoparticles has largely decreased relative to the surface of the filter paper. By the increasing of the depth, there is almost no electric field enhancement effect. Besides, those metal nanoparticles outside of the DOF cannot receive the enhanced Raman signal. Therefore, those metal nanoparticles outside of the DOF do not contribute to the Raman signal enhancement. It can be seen from this simulation, only the metal nanoparticles inside the Raman measuring DOF (several hundred nanometers to micro meters) can enhance the electric field. Thus, by the optical simulation, proving that the metal nanoparticles of the SERS substrate produced by the dip coating method have very low Raman signal enhancement efficiency, and the production process is not cost effectiveness either. Thus, compared to the conventional method, the disclosed example uses laser thermal annealing to produce the SERS substrate, the metal nanoparticles can be high efficiently produced on the paper and have good Raman signal enhancement.

Figure 17:
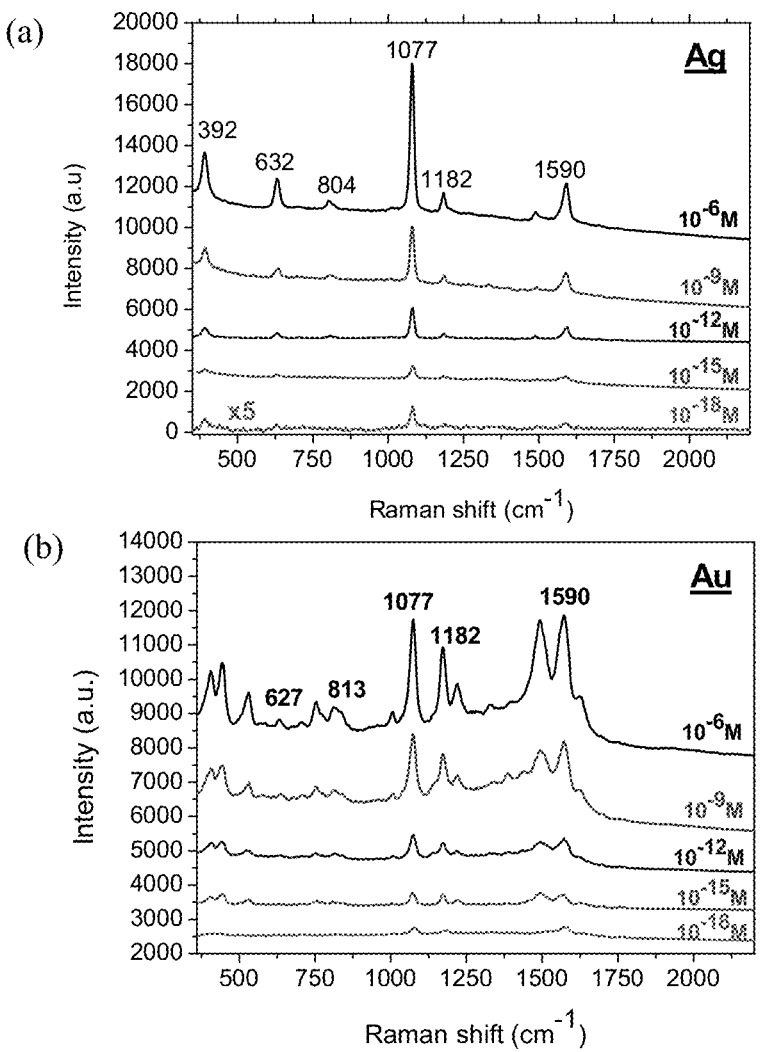
FIG. 17 shows detecting the SERS spectrum (a) silver nanoparticle (b) gold nanoparticle of each concentration of 4-Amino thiophenol (4-ATP) by a SERS substrate made by the parameter of the preferred example of the first embodiment.

The SERS substrate using paper base according to all the embodiment of the disclosed example can detect very small concentration range. As shown in FIG. 17, using the SERS substrate prepared by the optimized parameter of the first embodiment of the disclosed example (metal film thickness 30 nm under one shot of laser ablation) to do the Raman signal measuring of each concentration of the 4-amino thiophenol. In the Raman spectrum, even the concentration of silver nanoparticles or gold nanoparticles is as low as $10^{-18}$ M, the characteristic peaks 1077 cm$^{-1}$ and 1575 cm$^{-1}$ of the 4-amino thiophenol still have significant signals. In the measuring, dropping 20 µL of water onto the substrate and let the water naturally dry out, and concentrating the water into a small spot area with 4 mm diameter. If the concentration of the analyte dropped is $10^{-8}$ M, there are 12 molecular in the spot area, which can be deemed as single molecular testing.

Besides, everywhere on the surface of the paper base of all the embodiments in the disclosed example can obtain $2\times10^{10}$ ultra high enhancement factor. Therefore, even under lower concentration and the solute of the analyte is not evenly distributed, the analyte signal can still be measured by the Raman mapping since the Raman scattering substrate with paper base has high density and evenly distributed hot spots. Therefore, it is proved that the SERS substrate formed by applying laser thermal annealing on the paper base has very high sensitivity. The excellent Raman signal enhancement comes from the densely arranged metal nanoparticles on the quasi 3D structure which creates nano scale distance among the nanoparticles.

Figure 18:
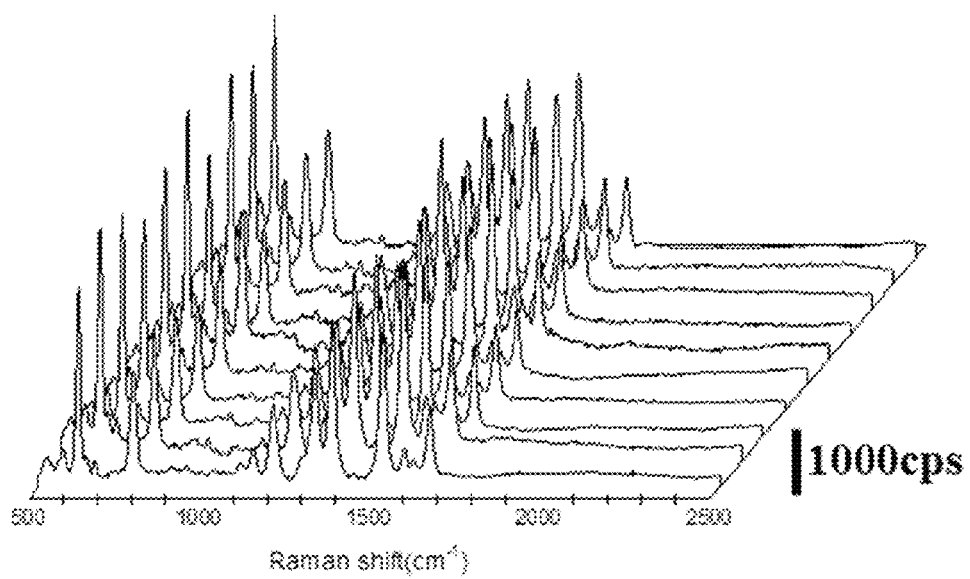
FIG. 18 shows the preferred example of the first embodiment; the silver nanoparticle SERS substrate is detected at different spots randomly on the same substrate to get the Raman spectrum at rhodamine concentration $10^{-5}$ M.

A good SERS base not only need to have good signal enhancing ability, but also need to have good signal reproducibility. Therefore, in order to evaluate the signal reproducibility of the paper based SERS substrate of all the embodiments, a SERS substrate produced according to the optimized parameter as shown in the first embodiment is tested. Using $10^{-5}$ M rhodamine solution (R6G), and randomly selecting 10 different areas which space apart with 5 µm distance from a 50 µm$^2$ area of the same substrate to do the Raman signal measuring, as shown in FIG. 18. As can be seen from the FIG. 18, the Raman signals collected from anywhere of the substrate have good uniformity.

The SERS substrate prepared by the aforementioned process can measure an atomic scale concentration as low as $10^{-18}$ M, and also has good reproducibility. By using the low-price paper which has the features of flexibility, disposability, and bio-degradability as the low thermal conduction base, a low-cost SERS substrate is provided. The SERS substrate has a very bright future in the biomedical field after being commercialized.

Although the disclosed example has been described with reference to the foregoing preferred embodiments, it will be understood that the invention is not limited to the details thereof. Various equivalent variations and modifications can still occur to those skilled in this art in view of the teachings of the disclosed example. Thus, all such variations and equivalent modifications are also embraced within the scope of the invention as defined in the appended claims.

What is claimed is:

1. A surface-enhanced Raman scattering substrate, comprising:
    a low thermal conductivity substrate having a first surface and a second surface, and the first surface having a plurality of ripple micro/nano structures; and
    a plurality of metal nanoparticles non-continuously and densely arranged on the ripple micro/nano structures of the first surface,
    wherein the metal nanoparticles have a height difference along the ripple micro/nano structures, and the metal nanoparticles form a 3D electric field enhanced region,
    wherein the 3D electric field enhanced region decreases from the first surface toward the second surface.

2. The surface-enhanced Raman scattering substrate as claimed in claim 1, wherein the space density distribution of the plurality of metal nanoparticles decreases from the first surface toward the second surface, and an electric field enhanced intensity of the 3D electric field enhanced region decreases toward the second surface.

3. The surface-enhanced Raman scattering substrate as claimed in claim 1, wherein the height difference of the ripple micro/nano structures is 100 nm-10 um.

4. The surface-enhanced Raman scattering substrate as claimed in claim 1, wherein a thermal conductivity of the low thermal conductivity substrate is 0.15 W/mK.

5. The surface-enhanced Raman scattering substrate as claimed in claim 4, wherein the low thermal conductivity substrate is paper or oxide substrate.

6. The surface-enhanced Raman scattering substrate as claimed in claim 4, wherein the low thermal conductivity substrate is paper and has a plurality of fiber structures.

7. The surface-enhanced Raman scattering substrate as claimed in claim 1, further comprising a plurality of non-enhanced metal nanoparticles not distributed in the 3D electric field enhanced region, the amount of a plurality of enhanced metal nanoparticles distributed in the 3D electric field enhanced region is larger than the non-enhanced metal nanoparticles.

8. The surface-enhanced Raman scattering substrate as claimed in claim 1, wherein the plurality of metal nanoparticles distributed in the 3D electric field enhanced region has the effect of localized surface plasmon resonance.

9. The surface-enhanced Raman scattering substrate as claimed in claim 8, wherein the plurality of metal nanoparticles comprise metal oxides and combinations thereof, wherein the metals of the metal oxides is selected from a group consisting of gold, silver, platinum, aluminum, and copper.

* * * * *